United States Patent
Faison, Jr. et al.

(10) Patent No.: US 7,367,334 B2
(45) Date of Patent: *May 6, 2008

(54) FLUID VAPORIZING DEVICE HAVING CONTROLLED TEMPERATURE PROFILE HEATER/CAPILLARY TUBE

(75) Inventors: Gene G. Faison, Jr., Richmond, VA (US); Rajiv Gupta, Glen Allen, VA (US); Douglas D. McRae, Chesterfield, VA (US); Walter A. Nichols, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 713 days.

This patent is subject to a terminal disclaimer.

(21) Appl. No.: 10/648,282

(22) Filed: Aug. 27, 2003

(65) Prior Publication Data

US 2005/0045179 A1 Mar. 3, 2005

(51) Int. Cl.
*A61M 11/00* (2006.01)
(52) U.S. Cl. .................. 128/203.12; 392/390; 392/397
(58) Field of Classification Search ........... 128/200.14, 128/200.19, 200.21, 200.22, 200.23, 201.13, 128/203.16, 203.17, 203.23, 203.24, 203.26, 128/203.27, 204.17; 239/128, 134, 135; 219/540, 541; 392/390, 397, 311, 312, 313
See application file for complete search history.

(56) References Cited

U.S. PATENT DOCUMENTS

| 2,896,856 A | 7/1959 | Kravits |
| 3,084,698 A | 4/1963 | Smith |

(Continued)

FOREIGN PATENT DOCUMENTS

| BE | 354004 A | 9/1928 |

(Continued)

OTHER PUBLICATIONS

Notification of Transmittal of the International Search Report and the Written Opinion of the International Searching Authority, or the Declaration dated Dec. 21, 2004 for PCT/US2004/026613.

(Continued)

*Primary Examiner*—Steven O. Douglas
(74) *Attorney, Agent, or Firm*—Buchanan Ingersoll & Rooney PC

(57) ABSTRACT

A fluid vaporizing device useful for vaporizing fluid into an aerosol includes a capillary tube made from an electrically conductive material, an upstream electrode connected to the capillary tube, and a downstream electrode connected to the tube and provided with an electrical resistivity sufficient to cause heating of the downstream electrode during operation. According to various manufacturing techniques (a) the downstream electrode can be made of a material having a resistivity that is approximately constant over a desired temperature range, (b) the ratio of the resistance of the downstream electrode to the resistance of the capillary tube can be selected as a function of a preset liquid flow rate through the capillary tube, (c) the tuning range over which a desired quality aerosol can be produced can be selected to compensate for dimensional tolerances during mass production, and (d) the total hot resistance of the downstream electrode and capillary tube can be adjusted to control the location of a meniscus of a liquid vaporized in the capillary tube to produce a desired quality aerosol.

28 Claims, 8 Drawing Sheets

U.S. PATENT DOCUMENTS

| | | |
|---|---|---|
| 3,085,145 A | 4/1963 | Wray |
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,764,660 A | 8/1988 | Swiatosz |
| 4,776,515 A | 10/1988 | Michalchik |
| 4,790,305 A | 12/1988 | Zoltan et al. |
| 4,795,330 A * | 1/1989 | Noakes et al. ................. 425/6 |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Muller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,388,574 A | 2/1995 | Ingebrethsen |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,509,557 A | 4/1996 | Jimarez et al. |
| 5,515,842 A | 5/1996 | Ramseyer et al. |
| 5,522,385 A | 6/1996 | Lloyd et al. |
| 5,523,226 A * | 6/1996 | Wheeler ..................... 435/325 |
| 5,556,964 A | 9/1996 | Hofstraat et al. |
| 5,559,923 A | 9/1996 | Robelen |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,706,389 A | 1/1998 | Pohler |
| 5,730,158 A | 3/1998 | Collins et al. |
| 5,743,251 A * | 4/1998 | Howell et al. ......... 128/200.14 |
| 5,756,995 A | 5/1998 | Maswadeh et al. |
| 5,765,724 A | 6/1998 | Amberg et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,870,524 A | 2/1999 | Swiatosz |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |

| | | | |
|---|---|---|---|
| 6,014,970 A | 1/2000 | Ivri et al. | |
| 6,053,176 A | 4/2000 | Adams et al. | |
| 6,054,032 A | 4/2000 | Haddad et al. | |
| 6,069,214 A | 5/2000 | McCormick et al. | |
| 6,069,219 A | 5/2000 | McCormick et al. | |
| 6,070,575 A | 6/2000 | Gonda et al. | |
| 6,071,428 A | 6/2000 | Granks et al. | |
| 6,071,554 A | 6/2000 | Isomura et al. | |
| 6,076,522 A | 6/2000 | Dwivedi et al. | |
| 6,077,543 A | 6/2000 | Gordon et al. | |
| 6,080,721 A | 6/2000 | Patton | |
| 6,085,740 A | 7/2000 | Ivri et al. | |
| 6,085,753 A | 7/2000 | Gonda et al. | |
| 6,089,228 A | 7/2000 | Smith et al. | |
| 6,095,153 A | 8/2000 | Kessler et al. | |
| 6,098,615 A | 8/2000 | Lloyd et al. | |
| 6,098,620 A | 8/2000 | Lloyd et al. | |
| 6,103,270 A | 8/2000 | Johnson et al. | |
| 6,116,516 A | 9/2000 | Ganan-Calvo | |
| 6,116,893 A | 9/2000 | Peach | |
| 6,119,953 A | 9/2000 | Ganan-Calvo et al. | |
| 6,123,068 A | 9/2000 | Lloyd et al. | |
| 6,123,936 A | 9/2000 | Platz et al. | |
| 6,131,567 A | 10/2000 | Gonda et al. | |
| 6,131,570 A | 10/2000 | Schuster et al. | |
| 6,136,346 A | 10/2000 | Eljamal et al. | |
| 6,138,668 A | 10/2000 | Patton et al. | |
| 6,155,268 A | 12/2000 | Takeuchi | |
| 6,158,431 A | 12/2000 | Poole | |
| 6,158,676 A | 12/2000 | Hughes | |
| 6,159,188 A | 12/2000 | Laibovitz et al. | |
| 6,164,630 A | 12/2000 | Birdsell et al. | |
| 6,165,463 A | 12/2000 | Platz et al. | |
| 6,167,880 B1 | 1/2001 | Gonda et al. | |
| 6,174,469 B1 | 1/2001 | Ganan-Calvo | |
| 6,182,712 B1 | 2/2001 | Stout et al. | |
| 6,187,214 B1 | 2/2001 | Ganan-Calvo | |
| 6,187,344 B1 | 2/2001 | Eljamal et al. | |
| 6,189,453 B1 | 2/2001 | Lin | |
| 6,189,803 B1 | 2/2001 | Ganan-Calvo | |
| 6,192,882 B1 | 2/2001 | Gonda | |
| 6,197,835 B1 | 3/2001 | Ganan-Calvo | |
| 6,205,999 B1 | 3/2001 | Ivri et al. | |
| 6,206,242 B1 | 3/2001 | Amberg et al. | |
| 6,207,135 B1 | 3/2001 | Rossling et al. | |
| 6,223,746 B1 | 5/2001 | Jewett et al. | |
| 6,230,706 B1 | 5/2001 | Gonda et al. | |
| 6,231,851 B1 | 5/2001 | Platz et al. | |
| 6,234,167 B1 | 5/2001 | Cox et al. | |
| 6,234,402 B1 | 5/2001 | Ganan-Calvo | |
| 6,235,177 B1 | 5/2001 | Borland et al. | |
| 6,250,298 B1 | 6/2001 | Gonda et al. | |
| 6,257,233 B1 | 7/2001 | Burr et al. | |
| 6,258,341 B1 | 7/2001 | Foster et al. | |
| 6,263,872 B1 | 7/2001 | Schuster et al. | |
| 6,267,155 B1 | 7/2001 | Parks et al. | |
| 6,275,650 B1 | 8/2001 | Lambert | |
| 6,276,347 B1 | 8/2001 | Hunt | |
| 6,284,525 B1 | 9/2001 | Mathies et al. | |
| 6,288,360 B1 | 9/2001 | Beste | |
| 6,290,685 B1 | 9/2001 | Insley et al. | |
| 6,294,204 B1 | 9/2001 | Rossling et al. | |
| 6,295,986 B1 | 10/2001 | Patel et al. | |
| 6,318,361 B1 | 11/2001 | Sosiak | |
| 6,491,233 B2 * | 12/2002 | Nichols | 239/128 |
| 6,501,052 B2 * | 12/2002 | Cox et al. | 219/486 |
| 6,528,018 B1 | 3/2003 | Berndt | |
| 6,568,390 B2 * | 5/2003 | Nichols et al. | 128/203.16 |
| 6,640,050 B2 * | 10/2003 | Nichols et al. | 392/390 |
| 6,684,879 B1 * | 2/2004 | Coffee et al. | 128/200.14 |
| 6,772,757 B2 * | 8/2004 | Sprinkel, Jr. | 128/203.26 |
| 7,147,170 B2 * | 12/2006 | Nguyen et al. | 239/13 |
| 2001/0032647 A1 | 10/2001 | Schuster et al. | |
| 2004/0025865 A1 * | 2/2004 | Nichols et al. | 128/200.14 |
| 2004/0265519 A1 * | 12/2004 | Pellizzari et al. | 428/34.1 |

FOREIGN PATENT DOCUMENTS

| | | |
|---|---|---|
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 216121 B | 3/1991 |
| HU | 207457 A | 4/1993 |
| HU | P953409 | 6/1994 |
| HU | 168128 B | 11/1997 |
| WO | 98/17131 | 4/1994 |
| WO | 94/09842 A | 5/1994 |
| WO | 03/028409 A1 | 4/2003 |
| WO | 03/037412 A2 | 5/2003 |
| WO | 03/049535 A1 | 6/2003 |

OTHER PUBLICATIONS

Barry, P.W. et al. "In Vitro Comparison of the Amount of Salbutamol Available for Inhalation From Different Formulations Used with Different Spacer Devices" Eur Respir J 1997; 10:1345-1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477-7505, May-Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp. 97-102.

Hou, Shuguang et al. Solution Stability of Budensonide in Novel Aerosol Formulations Abstract No. 2582. Solid State Physical Pharmacy, Nov. 17, 1998, p. S-307.

Kousaka, Yasuo et al., "Generation of Aerosol Particles by Boiling of Suspensions", Aerosol Science and Technology, 21:236-240 (1994) (023).

Moren, Folke "Drug Deposition of Pressurized Inhalation Aerosols I. Influence of Actuator Tube Design" AB Draco (Subsidiary of AB Astra, Sweden) Research and Development Laboratories Pack, S-221 01 Lund (Sweden), International Journal of Pharmaceutics, 1 (1978) 205-212.

Newman, Stephen P. et al. "Deposition of Pressurized Suspension Aerosols Inhaled Through Extension Devices.sup. 1-3 " Am Rev Respir Dis 1981; 124:317-320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766-770, Jul. 1980.

Notification of Transmittal of the International Search Report or the Declaration dated Feb. 14, 2003 for PCT/US02/28703.

Written Opinion for PCT/US02/28703 dated Jul. 8, 2003.

* cited by examiner

FLUID VAPORIZING DEVICE HAVING CONTROLLED TEMPERATURE PROFILE HEATER/CAPILLARY TUBE

BACKGROUND

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, distributing insecticides and delivering paint and lubricant.

Commonly owned U.S. Pat. Nos. 5,743,251 and 6,234,167, which are hereby incorporated by reference in their entireties, disclose aerosol generators, along with certain principles of operation and materials used in an aerosol generator, as well as methods of producing an aerosol, and an aerosol.

SUMMARY

A fluid vaporizing device is provided, which is operable to produce an aerosol. In a preferred embodiment, the fluid vaporizing device comprises a capillary tube including an inlet and an outlet, and being of a material having a first resistivity; a first electrode connected to the capillary tube; and a second electrode connected to the capillary tube closer to the outlet of the capillary tube than the first electrode. The second electrode is preferably of a material having a resistivity which is (i) higher than the resistivity of the capillary tube material at ambient temperature, and (ii) is substantially constant between ambient temperature and at least about 100° C. A preferred material for the second electrode is a nickel-base alloy containing 19-21 weight % Cr.

Another preferred embodiment of the fluid vaporizing device comprises a capillary tube having a resistance Rc; a first electrode connected to the capillary tube; and a second electrode connected to the capillary tube closer to the outlet of the capillary tube than the first electrode, and the second electrode having a resistance Re. The relationship between Rc and Re is such that the fluid vaporizing device has a resistance ratio $Rr=Re/Rc$, wherein Rr has a preset value corresponding to a preset flow rate of liquid through the capillary tube, the resistance ratio Rr decreasing as the preset flow rate increases.

Another preferred embodiment of the fluid vaporizing device comprises a resistively heated capillary tube having a resistance Rc which increases as the capillary tube is heated; a first electrode connected to the capillary tube; and a second electrode connected to the capillary tube closer to the outlet of the capillary tube than the first electrode, the second electrode (including any contact material joining the second electrode to the capillary tube) having a resistance Re which increases as the second electrode is heated. The vaporized fluid is generated by passing electrical current through a section of the capillary tube between the first and second electrodes while supplying liquid to the inlet of the capillary tube, the liquid being heated in the capillary tube and forming the vaporized fluid downstream of a meniscus at which liquid passing through the capillary tube is converted to vapor, the fluid vaporizing device having a total hot resistance $Rt=Rc+Re$ during delivery of the vaporized fluid, wherein Rt has a preset value effective to provide the meniscus in a portion of the capillary tube spaced from the outlet by a predetermined distance.

A preferred method of manufacturing fluid vaporizing devices comprises a) making a first fluid vaporizing device by metallurgically bonding a first electrode to a stainless steel capillary tube having a resistance Rc1, metallurgically bonding a second electrode to the capillary tube closer to an outlet of the capillary tube than the first electrode, the second electrode having a resistance Re1 (including any contact material joining the second electrode to the capillary tube), the first fluid vaporizing device being operable to produce vaporized fluid by supplying a liquid to the capillary tube through an inlet thereof, and applying a voltage across the first electrode and second electrode to heat the liquid in the capillary tube to a sufficient temperature to form a vapor which exits the capillary tube through the outlet, b) making a second fluid vaporizing device by metallurgically bonding a first electrode to a stainless steel capillary tube having a resistance Rc2, metallurgically bonding a second electrode to the capillary tube closer to an outlet of the capillary tube than the first electrode, the second electrode having a resistance Re2 (including any contact material joining the second electrode to the capillary tube), the second fluid vaporizing device being operable to produce vaporized fluid by supplying a liquid to the capillary tube through an inlet thereof, and applying a voltage across the first electrode and second electrode to heat the liquid in the capillary tube to a sufficient temperature to form a vapor which exits the capillary tube through the outlet, and c) wherein the first and second fluid vaporizing devices have a total hot resistance $Rt=Rc+Re$ during delivery of the vaporized fluid and a tuning range $TR \geq 10$ m$\Omega$ which equals the difference of a maximum hot resistance value Rmax and a minimum hot resistance value Rmin at which the capillary tube can be heated to produce a desired quality aerosol, the tuning range of the second fluid vaporizing device at least partially overlapping the tuning range of the first fluid vaporizing device, and the first and second fluid vaporizing devices having capillary tubes and/or second electrodes which are not identical in size, the first and second fluid vaporizing devices having the same target resistance during operation thereof and the target resistance being within the tuning ranges of the first and second fluid vaporizing devices.

DESCRIPTION OF THE PREFERRED EMBODIMENTS

Figure 1:
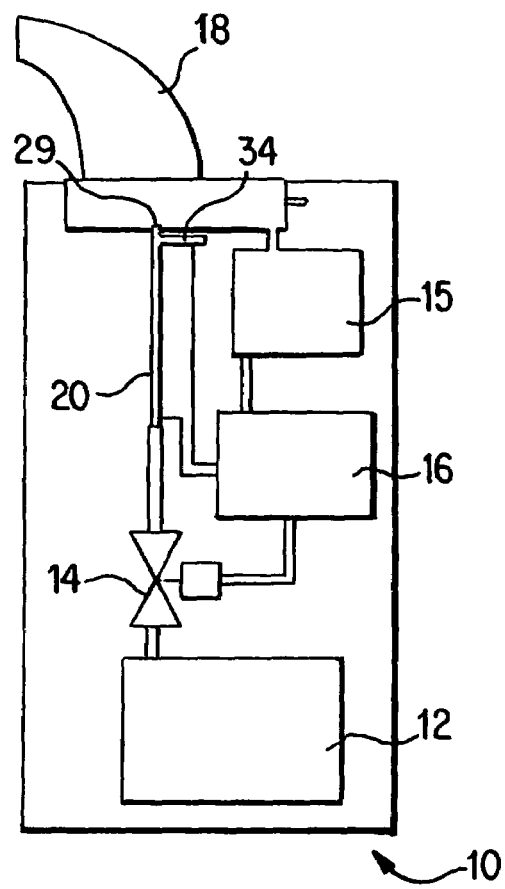
FIG. 1 illustrates a fluid vaporizing device according to an embodiment of the invention.

The invention provides a fluid vaporizing device useful for applications including aerosol generation. The device includes a heater/capillary tube having a flow passage with an inlet, an outlet, and at least two electrodes connected to electrically conductive material of the capillary tube at spaced points along the flow passage between the inlet and the outlet. The flow passage is defined by the interior of the capillary tube, which is preferably made from an electrically conductive material such as stainless steel. A section of the capillary tube between the inlet and a first electrode constitutes a feed section, and a section of the capillary tube between the first and second electrodes constitutes a heated section. A voltage applied between the first and second electrodes generates heat in the heated section based on the resistivity of the stainless steel or other electrically conductive material forming the capillary tube, as well as the cross-sectional area and the length of the heated section.

An aerosol can be formed from a liquid using a heated capillary by supplying liquid under pressure to an upstream end of the flow passage at an inlet to the capillary tube, and passing the liquid through the feed section of the capillary tube into the heated section. When the liquid is flowing through the capillary tube, as it enters the heated section, initially the liquid is heated and heat transfer to the fluid from the heated capillary tube is high. As the heated liquid continues to move along the heated section toward the outlet or tip of the capillary tube, the liquid is converted to a vapor. The coefficient of heat transfer from the wall of the heated capillary tube to the vapor is low. As a result, the wall temperature of the capillary tube in the heated section toward the outlet or tip of the capillary tube increases relative to the upstream portion of the tube. However, if the electrode at the tip of the capillary acts as a heat sink, it may be more difficult to maintain the temperature of the vapor exiting from the tip of the capillary tube at the optimum temperature for producing aerosol having the desired aerosol droplet size.

In order to improve the temperature profile of the capillary tube, the electrode at the downstream or exit end of the heated section according to an embodiment of the present invention is provided with a predetermined electrical resistance which causes the electrode to heat up when voltage is applied, and thereby minimize a temperature gradient between the wall of the capillary tube at the downstream end of the heated section and the downstream electrode. The electrical resistivity, cross-sectional area, and length of the electrode at the downstream end of the heated section can be selected to minimize or eliminate the above-mentioned temperature gradient and prevent the downstream electrode from acting as a heat sink, thereby minimizing loss of heat from the downstream end of the heated section. The electrical resistivity of the downstream electrode that achieves the optimum balancing of heat transfer along the capillary tube may be selected to accommodate changes in the thermal profile as a function of the desired flow rate of fluid and/or vapor through the tube.

By minimizing the loss of heat from the downstream end of the heated section, a desired exit temperature for the vapor leaving the heated section can be maintained without having to heat the fluid flowing through the intermediate portions of the heated section to as high a temperature as in the case where the downstream electrode conducts heat away from the tip of the capillary tube. This feature provides a significant advantage over a heated capillary tube where the downstream electrode has a very low electrical resistance. In a heated capillary tube where the downstream electrode has a very low electrical resistance, the electrode will have a temperature significantly lower than the temperature at the wall of the downstream end of the heated section of the capillary tube and can act as a heat sink. If the downstream electrode acts as a heat sink, more heat must be input to the liquid passing through the capillary tube in order to maintain a desired temperature for the vapor exiting from the capillary tube. The resulting high temperatures of the fluid passing through the capillary tube can possibly lead to thermal degradation of the fluid especially in the case of vaporizing medicated fluids.

FIG. 1 shows an example of a fluid vaporizing device in the form of an aerosol generator 10 in accordance with one embodiment of the invention. As shown, the aerosol generator 10 includes a source 12 of fluid, a valve 14, a heated capillary passage 20, a mouthpiece 18, an optional sensor 15 and a controller 16. The controller 16 includes suitable electrical connections and ancillary equipment such as a battery which cooperates with the controller for operating the valve 14, the sensor 15 and supplying electricity to heat the capillary passage 20. In operation, the valve 14 can be opened to allow a desired volume of fluid from the source 12 to enter the passage 20, prior to or subsequent to detection by the sensor 15 of vacuum pressure applied to the mouthpiece 18 by a user attempting to inhale aerosol from the aerosol generator 10. As fluid is supplied to the passage 20, the controller 16 controls the amount of power provided to heat the fluid to a suitable temperature for volatilizing the fluid therein. The volatilized fluid exits the outlet of the passage 20, and the volatilized fluid forms an aerosol which can be inhaled by a user drawing upon the mouthpiece 18.

The aerosol generator shown in FIG. 1 can be modified to utilize different fluid supply arrangements. For instance, the fluid source can comprise a delivery valve which delivers a predetermined volume of fluid to the passage 20 and/or the passage 20 can include a chamber of predetermined size to accommodate a predetermined volume of fluid to be volatilized during an inhalation cycle. In the case where the passage includes a chamber to accommodate a volume of fluid, the device can include a valve or valves downstream of the chamber for preventing flow of the fluid beyond the chamber during filling thereof. If desired, the chamber can include a preheater arranged to heat fluid in the chamber such that a vapor bubble expands and drives the remaining liquid from the chamber into the passage 20. Details of such a preheater arrangement can be found in commonly-owned U.S. Pat. No. 6,491,233, the disclosure of which is hereby incorporated by reference. If desired, the valve(s) could be omitted and the fluid source 12 can include a delivery arrangement such as a syringe pump, which supplies a predetermined volume of fluid to the chamber or directly to the passage 20. The heater can be the walls of the capillary tube defining passage 20, arranged to volatilize the liquid in passage 20. The entire wall of the capillary tube defining passage 20 can be made from an electrically conductive material such as stainless steel, so that as a voltage is applied to the tube, the tube is heated by the flow of electric current through the tube. As an alternative, the tube could be made from a non-conductive or semi-conductive material, such as glass or silicon, the tube including a heater formed from a resistance heating material such as platinum (Pt).

In the case of manual operations, the sensor 15 can be omitted such as in the case where the aerosol generator 10 is operated manually by a mechanical switch, electrical switch or other suitable technique. Although the aerosol generator 10 illustrated in FIG. 1 is useful for medical uses, the principles of the device can also be used in an application for vaporizing a fuel.

According to one aspect of the present invention, a capillary aerosol generator is formed from a tube made entirely of stainless steel or other electrically conductive materials, or a non-conductive or semi-conductive tube incorporating a heater formed from an electrically conductive material, such as platinum. Two electrodes are connected at spaced positions along the length of the tube, with a feed section being defined between the inlet end of the tube and the upstream electrode, a heated section being defined between the two electrodes, and a tip section between the downstream electrode and the exit end of the tube. The electrodes can be, for example, wire segments. A voltage applied between the two electrodes generates heat in the heated section based on the resistivity of the stainless steel or other material making up the tube or heater, and other parameters such as the cross-sectional area and length of the heated section. Fluid can be supplied to the aerosol generator, preferably at a substantially constant pressure and/or in a predetermined volume of fluid, from a fluid source upstream of the tube. The fluid passes through the feed section of the capillary tube between the inlet and the first electrode. As the fluid flows through the capillary tube into the heated section between the first and second electrodes, the fluid is heated and converted to a vapor. The vapor passes from the heated section of the capillary tube to the tip of the capillary tube and exits from the outlet end of the capillary tube. If the volatilized fluid enters ambient air from the tip of the capillary tube, the volatilized fluid condenses into small droplets, thereby forming an aerosol preferably having a size of less than 10 µm, preferably 0.01 to µm or 1 to 2 µm. However, the fluid can comprise a liquid fuel which is vaporized in the tube and passed into a hot chamber in which the vapor does not condense into an aerosol. In a preferred embodiment, the capillary tube has an inner diameter of 0.1 to 0.5 mm, more preferably 0.2 to 0.4 mm, and the heated zone has a length of 5 to 40 mm, more preferably 10 to 25 mm.

As fluid initially enters the heated section of the capillary tube, transfer of heat to the fluid is high because there is a relatively high heat transfer coefficient between the fluid and the wall of the tube. As the heated fluid continues to move downstream along the heated section, the fluid is converted to a vapor. The heat transfer coefficient between the wall and the vapor is low. With less heat being transferred from the wall of the capillary tube to the vapor, the wall temperature of the capillary tube increases in the area containing vapor.

The wall temperature at the downstream end of the heated section is preferably maintained at a desired temperature by providing a downstream electrode which minimizes heat loss. For example, heat can be prevented from being conducted away from the tube by the downstream electrode in the case where the downstream electrode is provided with a high enough electrical resistance to generate sufficient heat to maintain the downstream end of the capillary tube wall at a desired temperature, thereby minimizing a temperature gradient and hence the driving force for heat conduction.

Figure 2:
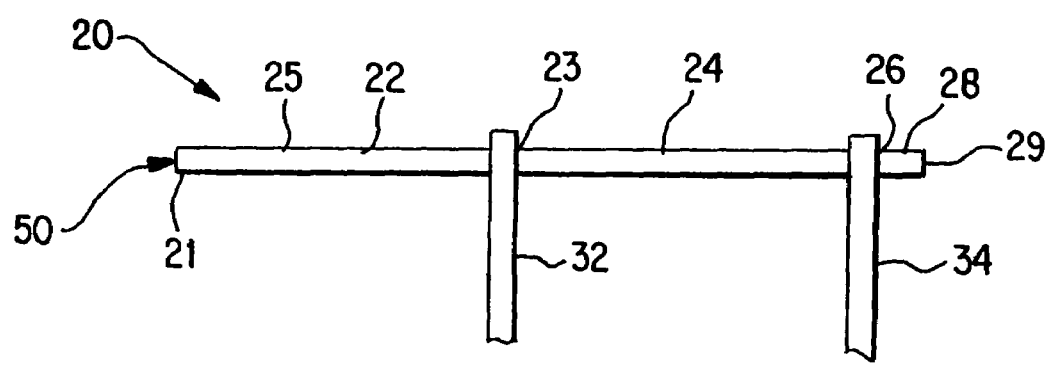
FIG. 2 is a schematic representation of a heated capillary tube according to an embodiment of the invention.

According to a first exemplary embodiment, as shown in FIG. 2, a capillary aerosol generator 20 includes a capillary tube 25 having an inlet end 21, an outlet end 29, and at least one upstream electrode 32 and one downstream electrode 34 connected to the capillary tube at points 23 and 26, respectively, by known means such as brazing or welding. The electrodes 32, 34 divide the capillary tube into an upstream feed section 22 between the inlet 21 and the first electrode 32, an intermediate heated section 24 between the first electrode 32 and the second electrode 34, and a downstream tip 28 defined between the second electrode 34 and the outlet end 29 of the capillary tube.

Fluid from a fluid source 50 is provided to the heated capillary tube through inlet end 21, e.g., fluid can be supplied in the form of a pressurized liquid. As the liquid passes through the capillary tube from the feed section 22 into the heated section 24, heat generated by passing an electrical current between the electrodes 32 and 34 is conducted to the liquid passing through the heated section. As the liquid continues downstream through the heated section, the liquid is converted to vapor by the input of heat. The heat transfer coefficient between the wall and the vapor is less than the heat transfer coefficient between the wall and the liquid. Therefore, the downstream portion of the capillary tube closer to the downstream electrode 34 is heated to a higher temperature than a portion of the tube closer to the upstream electrode 32. In order to prevent the mass of the downstream electrode 34 from acting as a heat sink that would conduct heat away from the capillary tube, the downstream electrode 34 is made from an electrically resistive material that provides a desired downstream electrode temperature during the application of electrical current through the electrodes 32, 34. The electrical resistivity of electrode 34, along with other parameters including its cross-sectional area and length can be chosen in order to minimize any heat sink effect that the electrode 34 may have on the capillary tube. The selection of these parameters can be a function of the desired flow rate of fluid/vapor through the capillary tube. At higher flow rates, more heat must be input to the heated section to maintain the desired exit temperatures for the vapor. Higher power input is required to maintain the preferred temperature profile as the flow rate is increased. Higher power requires a higher current in accordance with the relationship that power equals $I^2R$. Higher electrical current is needed in the fluid channel because of the higher heat dissipation rate at higher flow rates. However, unless the resistivity of the downstream electrode is changed, the higher power input may result in too much heat being generated at the downstream electrode. Therefore, at higher flow rates through the capillary tube, the resistance of the downstream electrode may actually be reduced while achieving the desired temperature to avoid any temperature gradient between the downstream electrode and the downstream end of the capillary tube. Accordingly, the temperature profile of the capillary tube along the heated section can be controlled and excessive heating of the fluid/vapor passing through the heated section can be avoided.

Figure 3:
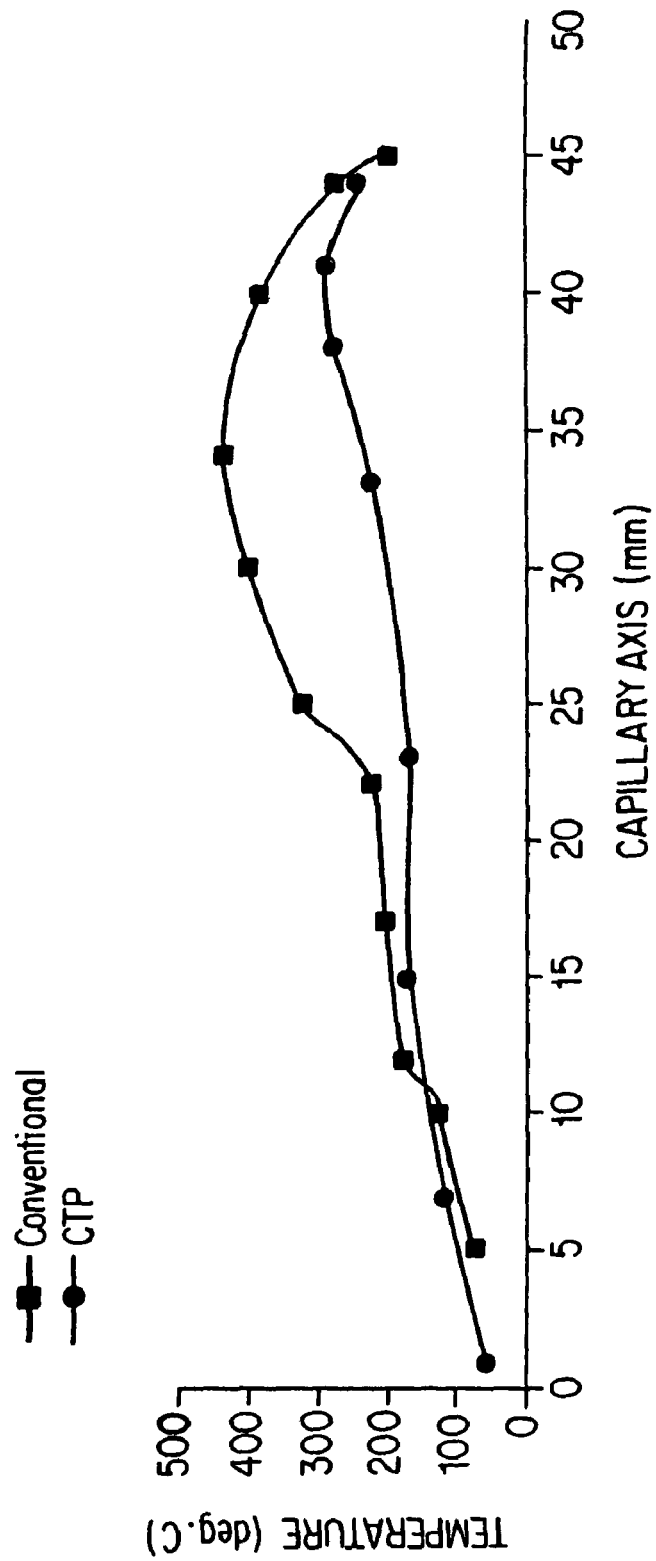
FIG. 3 illustrates wall temperature profiles for a comparative heated capillary tube and a heated capillary tube according to the present invention.

FIG. 3 illustrates a comparison of wall temperature profiles in an aerosol generator having electrodes of the same highly conductive material, and in the controlled temperature profile (CTP) aerosol generator according to the invention. The controlled temperature profile of the capillary tube along the heated section enables maintenance of a desired exit temperature for vapor leaving from the tip of the tube without overheating the fluid/vapor upstream thereof.

Another advantage that results from controlling the temperature profile along the capillary tube in medical applications is that the tip of the tube can more easily be maintained at a high enough temperature to optimize the formation of an aerosol with particles in the preferred range of less than 10 microns, preferably less than 5 microns in diameter, at which the particles in the form of droplets or solid particles are more effectively passed to the lungs of a user for delivery of medicaments.

From the foregoing, it will be apparent that the electrical resistance, cross-sectional area and length of the downstream electrode can be varied to achieve the desired temperature profile along the heated section of the capillary tube, with the resulting operational temperature of the downstream electrode balancing the temperature of the capillary tube near the tip, and thereby substantially eliminating any heat sink effect by the downstream electrode. For instance, the downstream electrode can comprise a 5 to 7 mm section of stainless steel tubing attached between the capillary tube and a low resistance wire completing the circuit to the power supply. The electrodes can be connected to the capillary tube using conventional methods (e.g., metallurgical bonding) that may include, but are not limited to, brazing, welding, and soldering, or the electrodes could be formed integrally with the capillary tube. In implementing the capillary heater in an inhaler, the capillary tube is preferably insulated and/or isolated from ambient air and the vapor emitted from the capillary tube. For example, an insulating material or a metal foil, such as stainless steel foil, could be used to support the capillary tip within a mouthpiece such that the vapor exiting the capillary tube does not contact the outer surface of the capillary tube upstream of the metal foil.

As described above, the capillary tube and the downstream electrode of the fluid vaporizing device each have an electrical resistance. For a given flow rate of liquid through the capillary tube, the resistance ratio, Rr, of the resistance of the downstream electrode, Re, to the resistance of the capillary tube, Rc, (i.e., Rr=Re/Rc), can be adjusted to provide a desired temperature profile along the capillary tube, and a desired quality aerosol with the fluid vaporizing device. The upstream electrode preferably has a much lower electric resistance than each of the downstream electrode and the capillary tube. Accordingly, the resistance of the upstream electrode is not used in determining the resistance ratio Rr. The upstream electrode is preferably made of copper to provide low resistance. Other materials having low resistance can alternatively be used.

The aerosol quality can be characterized in different ways. Particularly, the aerosol quality can be characterized by particle size distribution of the aerosol, and/or % recovery of one or more components of the aerosol. Regarding the particle size distribution, the mass of aerosol particles having a size less than some selected size can be used to characterize the aerosol quality. The selected particle size can be, for example, a size that facilitates deep lung penetration.

The aerosol recovery can be characterized by the "emitted dose," and/or the "respirable dose," of one or more component(s) of an aerosol. The component(s) can be one or more medicaments, for example. The "emitted dose" is defined herein as the ratio of the mass of the component(s) emitted by the fluid vaporizing device to a metered dose of the component(s) supplied to the capillary tube (i.e., emitted dose=[mass of component(s) emitted/metered dose]×100). The "respirable dose" is defined herein as the ratio of the mass of aerosol particles smaller than a selected size, x, to the emitted dose (i.e., respirable dose=[mass of aerosol particles<x/emitted dose]×100).

In accordance with one embodiment, the fluid vaporizing device is provided with a predetermined resistance ratio Rr of the resistance of the downstream electrode to the resistance of the capillary tube. The resistance of the downstream electrode and/or the capillary tube can be adjusted relative to each other to achieve a desired temperature profile of the capillary tube during operation of the fluid vaporizing device. The temperature profile can be monitored, for example, based on the uniformity of temperature at each location along the length of the capillary tube over time under operating steady state conditions, and/or on the period of time beginning from start up of the fluid vaporizing device to reach an operating temperature (e.g., a desired temperature of the tip). By controlling the temperature profile, it is possible to enhance aerosol formation and avoid thermal degradation of medicament to be aerosolized.

According to an embodiment of the fluid vaporizing device, the resistance ratio Rr that provides a high quality aerosol varies with the flow rate of the liquid through the capillary tube. Particularly, the resistance ratio Rr corresponding to a high quality aerosol decreases as the liquid flow rate through the capillary tube increases. For example, for a stainless steel capillary tube and a stainless steel downstream electrode, Rr is preferably about 10% to about 15% for a liquid flow rate of about 5 μL/sec, and about 7% to about 10% for a higher liquid flow rate of about 10 μL/sec.

The resistance ratio Rr can be varied by choice of resistance values of the downstream electrode and the capillary tube. For example, a predetermined value of the resistance ratio Rr can be achieved by providing a capillary tube having a selected resistance based on its composition and dimensions, and a downstream electrode having a certain resistance relative to the resistance of the capillary tube. The resistance R of a component of metallic material is given by: R=ρ·L/A, where ρ is the resistivity of the material, and L and A are the length and cross-sectional area, respectively, of the component. Accordingly, the length and/or cross-sectional area of the downstream electrode can be varied to provide the desired resistance of the downstream electrode, and thus the desired ratio Rr. For example, in order to decrease the resistance ratio Rr, the length L of the downstream electrode can be decreased, or its cross-sectional area A can be increased. Thus, depending on the desired flow rate through the capillary tube, the resistance ratio effective to provide optimal aerosol delivery can be achieved by selecting suitable materials and/or dimensions of the capillary and downstream electrode.

According to another embodiment, the downstream electrode is made of a material that has a resistivity that is higher at ambient temperature than the resistivity of the material of the capillary tube, and a substantially constant temperature coefficient of resistivity for the operating temperature range of the capillary tube. For example, the resistivity of the downstream electrode material can be substantially constant with respect to temperature up to at least about 100° C. The resistivity, ρ, of a material is temperature dependent and is given by: ρ=ρ$_0$(1+αΔT), where ρ$_0$ is the resistivity at a reference temperature, e.g., 20° C.; α is the temperature coefficient of resistivity; and ΔT is the temperature difference between the reference temperature and a temperature of interest.

A preferred material for the capillary tube is stainless steel. A preferred material for the downstream electrode is a nickel-base alloy sold under the brand NICHROME, a nickel-chromium alloy. A commercially available alloy sold under the brand NICHROME V contains, in weight %, 19 to 21% Cr, ≦0.15% C, ≦1% Fe, ≦2.5% Mn, 0.75 to 1.6% Si, ≦0.01% S, balance Ni; and commercially available alloy sold under the brand NICHROME 80/20 A has a nominal composition of 19.5% Cr, 0.40% Mn, 1.25% Si, 0.50% Fe, balance Ni. The NICHROME alloy has a higher ambient-temperature resistivity than stainless steel. In addition, the resistivity of the NICHROME alloy is substantially constant with respect to temperature; particularly the NICHROME alloy has a reported temperature coefficient of resistivity (TCR), α, of about $0.4 \times 10^{-3}$/° C. The NICHROME alloy can be heated up faster from ambient temperature than stainless steel due to the NICHROME alloy having a higher resistivity. Consequently, a steady state temperature can be achieved faster with the NICHROME alloy downstream electrode than for a stainless steel downstream electrode. By achieving a steady-state temperature faster at the downstream electrode, the tip of the capillary tube can be more quickly heated to a desired temperature, which avoids overheating the vaporized liquid passing through the tip.

According to a further embodiment, mass production of capillary heaters is facilitated by designing them with a predetermined "tuning range" as that term is defined herein. Due to variations in component materials and/or dimensions, challenges are presented in mass production of fluid vaporizing devices exhibiting desired performance characteristics. To address these challenges, it has been determined that desired performance characteristics can be achieved by manufacturing the fluid vaporizing devices with capillary tubes and downstream electrodes designed to be operated within a predetermined tuning range.

During operation of fluid vaporizing device, the hot resistances of the capillary tube and the downstream electrode of the fluid vaporizing device provide a total resistance, Rt. For a fluid vaporizing device having a stainless steel capillary tube and stainless steel downstream electrode, the total resistance increases with temperature from the ambient temperature value, referred to herein as the "cold resistance," due to changes in the resistivity of the capillary flow tube and/or downstream electrode of the fluid vaporizing device. It has been determined that when such fluid vaporizing devices are heated to produce vaporized fluid, the tuning range for the fluid delivery device is the difference between Rmin and Rmax over which good quality aerosol can be produced. In manufacture of fluid vaporizing devices, it is desirable that the capillary tube and downstream electrode be designed such that the target resistance (hot resistance at which the fluid vaporizing device is operated) lies within the tuning range, i.e., the "target resistance" of the fluid vaporizing device.

The values of Rmin and Rmax defining the tuning range for different fluid vaporizing devices may vary, for example, due to variations in the size of the downstream electrode, and/or the contact resistance of the connection between the downstream electrode and the capillary tube. For manufacturing purposes it is preferred that the tuning range for the fluid vaporizing devices be at least 10 mΩ. For example, a first fluid vaporizing device which supplies fluid at a predetermined flow rate can have an Rmin value of 800 mΩ, an Rmax value of 810 mΩ, and a tuning range of 10 mΩ. The target resistance for such first fluid vaporizing device can be set at a selected value between 800 mΩ and 810 mΩ, e.g., at 805 mΩ. This selected target resistance can be used as a manufacturing and operating specification for making and operating additional fluid vaporizing devices. Due to manufacturing tolerances, a second fluid vaporizing device may have, for example, an Rmin value of 795 mΩ, an Rmax value of 805 mΩ, and a tuning range of 10 mΩ. If the second fluid vaporizing device is operated at the target resistance of the first fluid vaporizing device, i.e., 805 mΩ, it will be capable of producing a good quality aerosol because the target resistance is within the tuning range. That is, the tuning ranges of the second fluid vaporizing device and the first fluid vaporizing device overlap each other and the target resistance.

It is desirable for the fluid vaporizing device to have a broad tuning range for manufacturing purposes. By providing a broad tuning range over which good quality aerosol can be produced, manufacturing tolerances for the fluid vaporizing device can be less stringent, which can in turn reduce manufacturing costs. In a preferred embodiment, the tuning range is at least about 10 mΩ, and more preferably at least about 20 mΩ. By increasing the tuning range, fluid vaporizing devices can be manufactured with greater manufacturing tolerances and the ability to be operated at a target resistance, which can be preset over a desired range.

Figure 4:
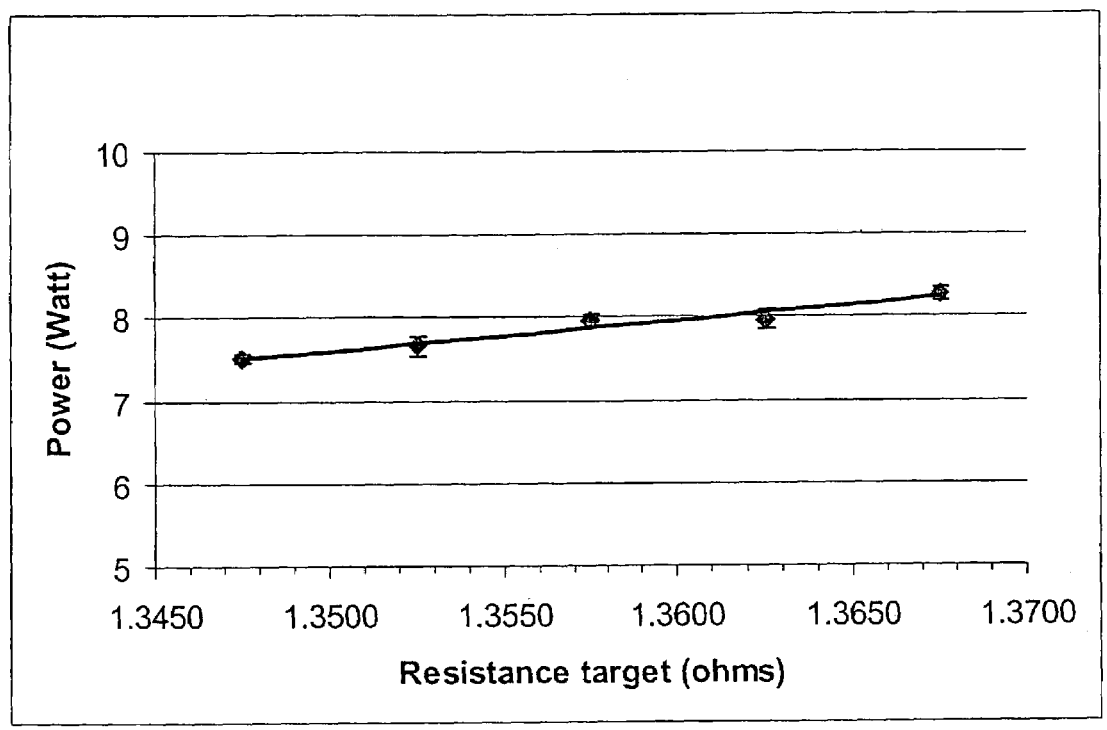
FIG. 4 shows the relationship between the applied power to the fluid vaporizing device and the resistance target.

FIG. 4 shows the relationship between the applied power and the target resistance for a fluid vaporizing device including a stainless steel capillary tube having a length of 35 mm, an internal diameter of 0.18 mm, and a wall thickness of 0.0015 inch, and a stainless steel downstream electrode welded to the capillary tube. As shown in FIG. 4, the tuning range of the fluid vaporizing device is about 20 mΩ.

Figure 5:
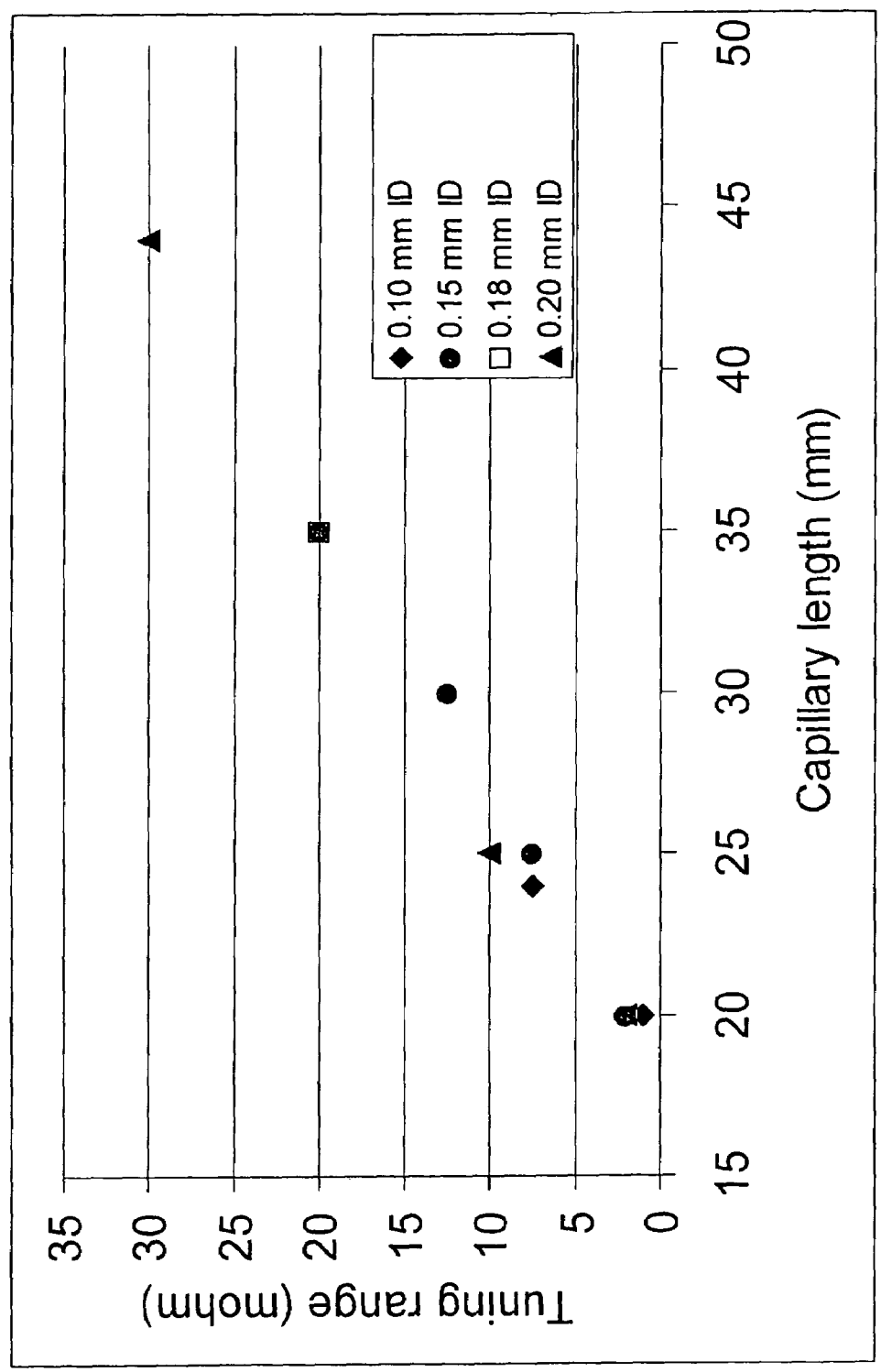
FIG. 5 shows a relationship between tuning range and length for capillary tubes having different internal diameters.

The tuning range can be changed by varying the length of the capillary tube, which changes the resistance of the capillary tube. FIG. 5 shows the relationship between the tuning range and the length of the capillary tube for capillary tube internal diameters of 0.10 mm, 0.15 mm, 0.18 mm, and 0.20 mm. The aerosol is formed using a 5% weight/weight oleyl alcohol (OA) in propylene glycol (PG) liquid formulation. The data show that the tuning range can be increased by increasing the capillary length. For example, a capillary tube having a length of 35 mm has a tuning range of 20 mΩ, while a capillary tube having a length of about 44 mm has a greater tuning range of 30 mΩ. FIG. 5 also shows that the minimum length of the capillary tube to provide a good quality aerosol using the OA/PG liquid formulation is about 20 mm.

FIG. 5 further shows that the internal diameter of the capillary flow passage does not significantly affect the tuning range at a given capillary length over the internal diameter range of 0.10 mm to 0.20 mm.

Figure 6:
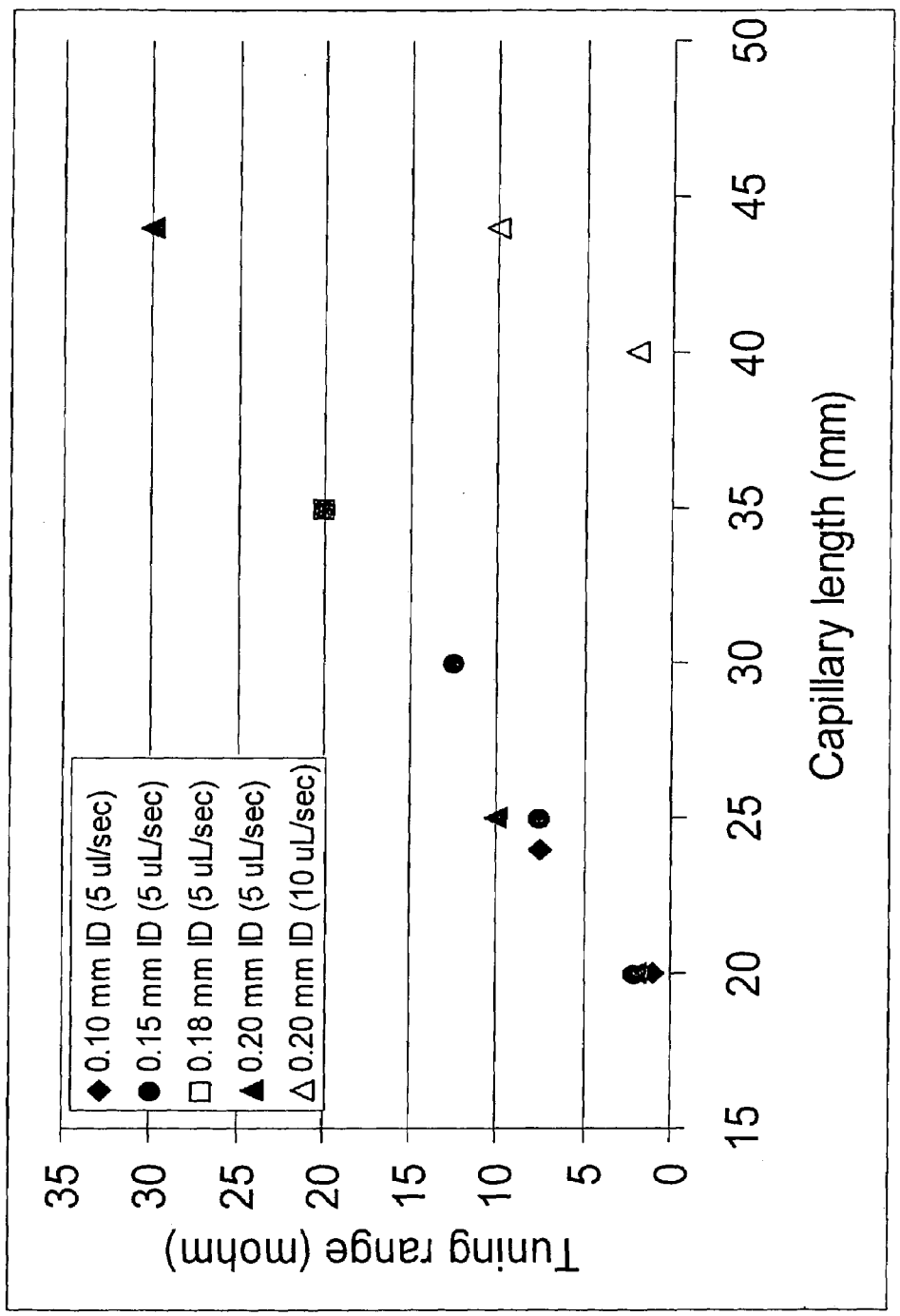
FIG. 6 shows a relationship between tuning range and length for capillary tubes having different internal diameters, at different liquid flow rates through the capillary tube.

FIG. 6 shows the relationship between the tuning range and the length of the capillary tube for internal diameters of 0.10 mm, 0.15 mm, 0.18 mm, and 0.20 mm at a liquid flow rate of 5 μL/sec, and for a capillary tube internal diameter of 0.20 mm at a liquid flow rate of 10 μL/sec. The aerosol is formed using a 5% weight/weight OA in PG liquid formulation. The data show that at a flow rate of 5 μL/sec, a good quality aerosol can be produced with a 20 mm length capillary tube having various internal diameters. For the OA/PG liquid formulation, the minimum capillary tube length to produce a good quality aerosol at a liquid flow rate of 10 μL/sec is about 40 mm, while it is only about 20 mm at a lower liquid flow rate of 5 μL/sec.

According to another embodiment, the fluid vaporizing device is designed to locate the meniscus of the liquid in the capillary tube at a desired location along the length of the capillary tube. During operation of the fluid vaporizing device, liquid passing through the capillary tube is heated such that liquid is converted to vapor in the vicinity of the meniscus and vapor exits the outlet of the capillary tube. The location of the meniscus of the liquid in the capillary tube can be controlled by varying the resistance target of the fluid vaporizing device. The location of the meniscus is defined herein as the furthest downstream location of liquid in contact with the inner surface of the capillary tube. Because the heat transfer coefficient between the capillary tube wall and vapor is low, the capillary tube downstream of the location of the meniscus can reach high temperatures resulting in overheating of the capillary tip. It is desirable that the meniscus be located close to the tip of the capillary tube to avoid overheating the capillary tip. The meniscus is preferably located upstream from the outlet to maximize vapor formation and minimize spraying of non-vaporized liquid from the outlet.

Figure 7:
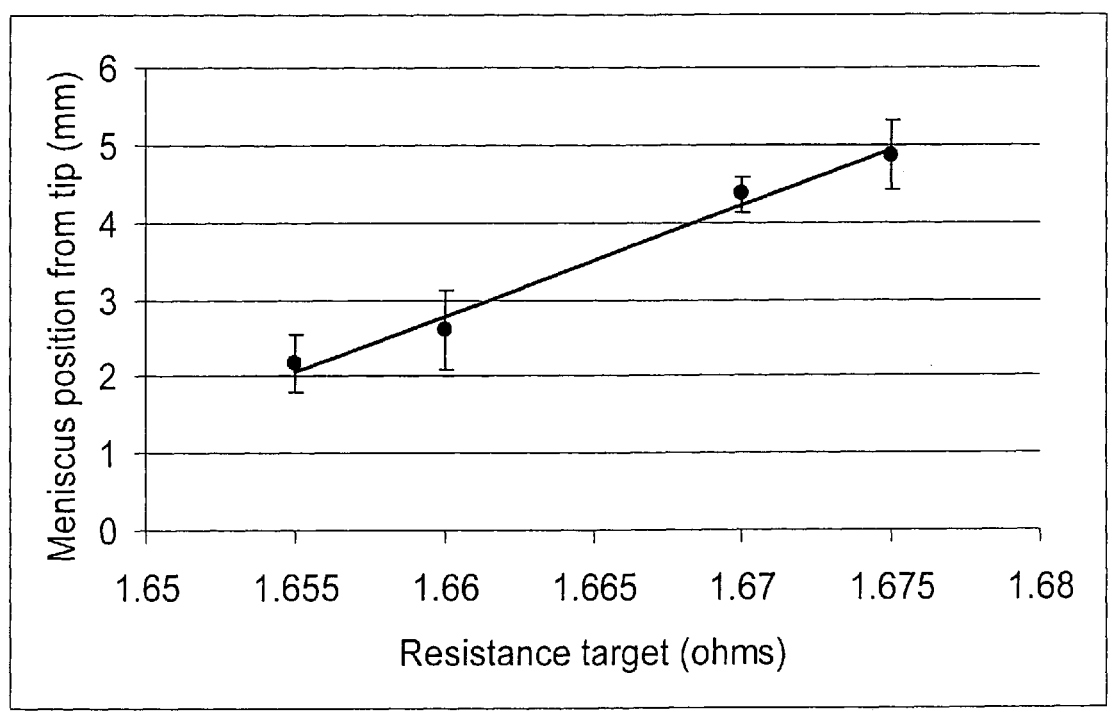
FIG. 7 shows a relationship between meniscus location and resistance target for a capillary tube having a length of 35 mm.

FIG. 7 shows a relationship between meniscus location relative to the outlet of a capillary tube having a length of 35 mm and the resistance target during formation of an aerosol using a 5% weight/weight OA in PG formulation. The data show that the meniscus moves upstream (i.e., away from the tip) as the target resistance is increased. The target resistance range from 1.655 Ω to 1.675 Ω provides 20 mΩ tuning range for the capillary tube over which a good quality aerosol is produced. The meniscus position from the outlet ranges from about 2 mm to about 5 mm over the tuning range. In a preferred embodiment, the meniscus position from the outlet is less than 5 mm, more preferably from about 2 mm to about 3 mm from the outlet. The ratio of the meniscus position from the outlet of about 2 mm to about 5 mm to the length of the capillary tube is from about 5% to about 15% of the capillary tube length of 35 mm.

Figure 8:
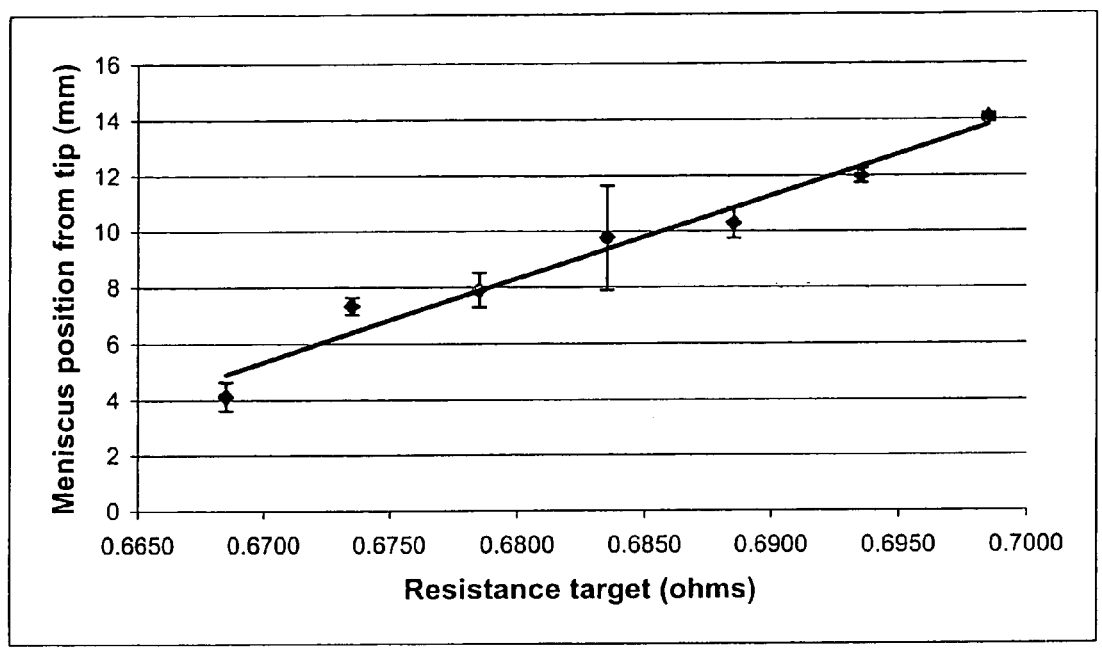
FIG. 8 shows a relationship between meniscus location and resistance target for a capillary tube having a length of 44 mm.

FIG. 8 shows a relationship between the meniscus position from the outlet of a capillary tube having a length of 44 mm and the resistance target during formation of an aerosol using a 5% weight/weight OA in PG formulation. The target resistance range of about 0.6685 Ω to about 0.6985 Ω represents a 30 mΩ tuning range for the capillary tube. The meniscus position from the outlet ranges from about 4 mm to about 14 mm over the tuning range. In a preferred embodiment, the meniscus position from the outlet is less than 14 mm. The ratio of the meniscus position from the outlet of about 4 mm to about 14 mm to the length of the capillary tube is from about 10% to about 30% for the capillary tube length of 44 mm.

Comparing FIGS. 7 and 8, a ratio of the meniscus position from the outlet to the length of the capillary tube of from about 5% to about 30%, or a meniscus position from the outlet of from about 2 mm to about 14 mm, provides a good quality aerosol for a capillary tube length of 35 mm or 44 mm.

Figure 9:
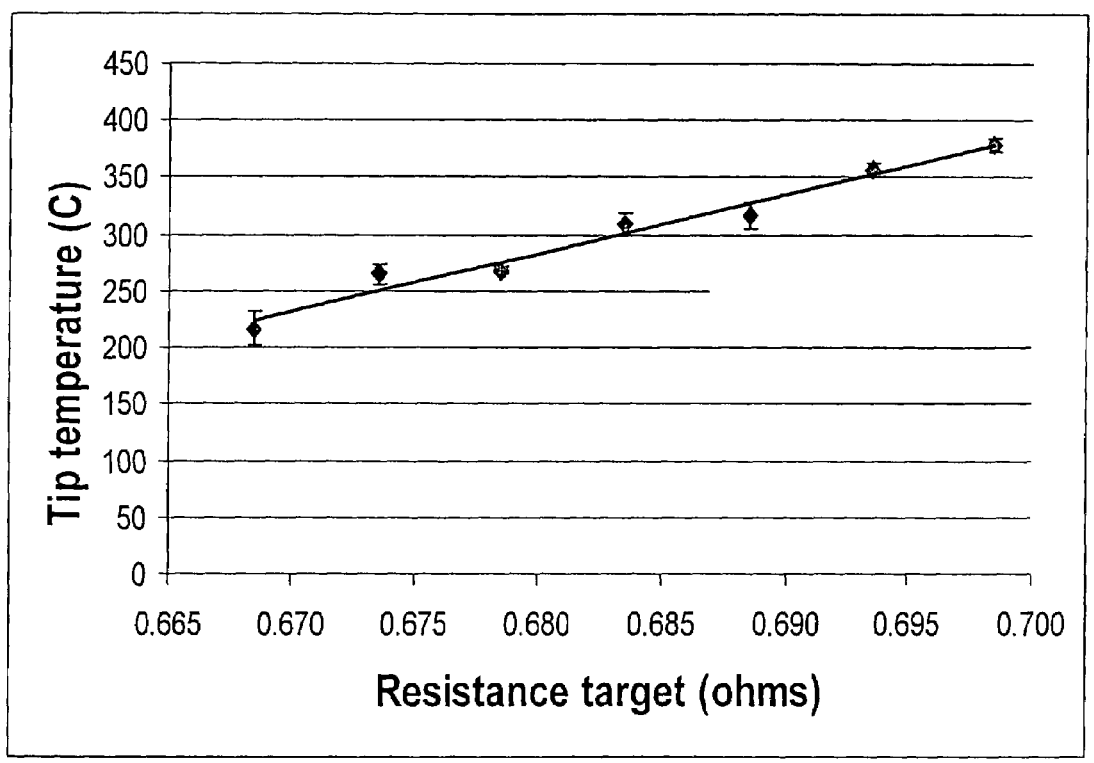
FIG. 9 shows a relationship between temperature of the tip of a capillary tube and the resistance target.

Increasing the tip temperature of the capillary tube causes the meniscus to move upstream. FIG. 9 shows that the tip temperature increases linearly with increasing resistance target. The tip temperature can be controlled by adjusting the resistance target in order to achieve an optimum location of the meniscus to produce a good quality aerosol and prevent superheating of the vapor. As described above, the resistance target can be adjusted by varying the resistance of the capillary tube and/or the downstream electrode.

The material to be vaporized can be a solution, suspension, emulsion or gel. For solutions and emulsions, the effect of the position of the meniscus from the outlet on the mass median aerodynamic diameter (MMAD) of the aerosol varies depending on whether the carrier of the liquid formulation is a condensation carrier (e.g., PG), or a non-condensation carrier (e.g., alcohol). More particularly, for a condensation carrier, as the meniscus moves upstream in the capillary tube, the MMAD increases. In contrast, for a non-condensation carrier, the MMAD decreases as the meniscus moves upstream.

While this invention has been illustrated and described in accordance with preferred embodiments, it is recognized that variations and changes may be made therein without departing from the spirit and scope of the invention as set forth in the claims.

What is claimed is:

1. A fluid vaporizing device, comprising:
   a capillary tube including an inlet and an outlet, the capillary tube being of a first material having a first resistivity;
   a first electrode connected to the capillary tube;
   a second electrode connected to the capillary tube closer to the outlet of the capillary tube than the first electrode, the second electrode being of a second material having a second resistivity which is (i) higher than the first resistivity at ambient temperature, and (ii) is substantially constant from ambient temperature to at least 100° C. or above.

2. The fluid vaporizing device of claim 1, wherein the second material is a Ni-Cr alloy.

3. The fluid vaporizing device of claim 2, wherein the first material is stainless steel and the Ni-Cr alloy includes 19 to 21 weight % Cr and at least 77 weight % Ni.

4. The fluid vaporizing device of claim 1, further comprising a mouthpiece, the outlet of the capillary tube directing vaporized fluid into the mouthpiece.

5. The fluid vaporizing device of claim 1, further comprising:
   a controller; and
   a sensor;
   wherein the sensor detects a delivery condition corresponding to delivery of a predetermined volume of aerosol, the controller being operable to effect delivery of a predetermined volume of liquid to the capillary tube when the delivery condition is sensed by the sensor and effect passage of electrical current through the capillary tube to volatilize liquid in the capillary tube.

6. A method of vaporizing a fluid, comprising:
   supplying a liquid into the capillary tube inlet of the fluid vaporizing device according to claim 1; and
   applying a voltage across the first electrode and second electrode to heat the liquid in the capillary tube to a sufficient temperature to form a vapor which exits the capillary tube through the outlet.

7. The method of claim 6, wherein the liquid comprises a medicament.

8. A method of manufacturing the fluid vaporizing device according to claim 1, comprising metallurgically bonding the second electrode to the capillary tube, the second electrode comprising a wire segment of a nickel-base alloy and the capillary tube comprising a section of stainless steel tubing.

9. In a fluid vaporizing device including a capillary tube including an inlet and an outlet, the capillary tube having a resistance Rc, a first electrode connected to the capillary tube, and a second electrode connected to the capillary tube closer to the outlet of the capillary tube than the first electrode, the second electrode having a resistance Re; the improvement comprising a relationship between Rc and Re such that the fluid vaporizing device has a resistance ratio Rr=Re/Rc, wherein Rr has a preset value corresponding to a preset flow rate of a liquid through the capillary tube, the preset value being at lower values when the preset flow rate is at higher values.

10. The fluid vaporizing device of claim 9, wherein Rr is from about 0.1 to about 0.15 when the preset flow rate is about 7.5 µL/sec or less.

11. The fluid vaporizing device of claim 9, wherein the capillary tube is a stainless steel tube and the second electrode is a stainless steel wire segment.

12. The fluid vaporizing device of claim 9, wherein Rr is from about 0.07 to about 0.1 when the preset flow rate is greater than 7.5 µL/sec.

13. The fluid vaporizing device of claim 9, further comprising a mouthpiece, the outlet of the capillary tube directing vaporized fluid into the mouthpiece.

14. The fluid vaporizing device of claim 9, further comprising:

a controller; and a sensor;

wherein the sensor detects a delivery condition corresponding to delivery of a predetermined volume of aerosol, the controller being operable to effect delivery of a predetermined volume of liquid to the capillary tube when the delivery condition is sensed by the sensor and to effect passage of electrical current through the capillary tube to volatilize liquid in the capillary tube.

15. A method of vaporizing a fluid, comprising:

supplying a liquid into the capillary tube through the inlet of the fluid vaporizing device according to claim 9; and applying a voltage across the first electrode and second electrode to heat the liquid in the capillary tube to a sufficient temperature to form a vapor which exits the capillary tube through the outlet.

16. The method of claim 15, wherein the liquid comprises a medicament.

17. A method of manufacturing the fluid vaporizing device according to claim 9, comprising metallurgically bonding the second electrode to the capillary tube, the second electrode comprising a wire segment of stainless steel and the capillary tube comprising a section of stainless steel tubing, the wire segment being sized to provide a hot resistance dependent on the preset flow rate of liquid to be supplied to the capillary tube.

18. A fluid vaporizing device for delivery of vaporized fluid, comprising:

a resistively heated capillary tube including an inlet and an outlet, the capillary tube being of material having a resistance Rc which increases as the capillary tube is heated;

a first electrode connected to the capillary tube; and a second electrode connected to the capillary tube closer to the outlet of the capillary tube than the first electrode, the second electrode having a resistance Re which increases as the second electrode is heated, wherein the vaporized fluid is generated by passing electrical current through a section of the capillary tube between the first and second electrodes while supplying liquid to the inlet of the capillary tube, the liquid being heated in the capillary tube and forming the vaporized fluid downstream of a meniscus at which liquid passing through the capillary tube is converted to vapor, the fluid vaporizing device having a total hot resistance Rt=Rc+Re during delivery of the vaporized fluid, wherein Rt has a preset value effective to provide the meniscus spaced from the outlet by a predetermined distance.

19. The fluid vaporizing device of claim 18, wherein the predetermined distance is less than about 5 mm.

20. The fluid vaporizing device of claim 18, wherein the predetermined distance is from about 4 mm to about 14 mm when the capillary tube has a length of at least 40 mm, and the predetermined distance is from about 2 mm to about 5 mm when the capillary tube has a length of less than 40 mm.

21. The fluid vaporizing device of claim 18, further comprising a mouthpiece, the outlet of the capillary tube directing vaporized fluid into the mouthpiece.

22. The fluid vaporizing device of claim 18, further comprising:

a controller; and a sensor;

wherein the sensor detects a delivery condition corresponding to delivery of a predetermined volume of aerosol, the controller being operable to effect delivery of medicament-containing liquid to the capillary tube when the delivery condition is sensed by the sensor and effect passage of electrical current through the capillary tube to volatilize the liquid in the capillary tube.

23. A method of manufacturing the fluid vaporizing device according to claim 18, comprising metallurgically bonding the second electrode to the capillary tube, the second electrode comprising a wire segment of stainless steel and the capillary tube comprising a section of stainless steel tubing, the capillary tube and/or second electrode being sized to provide $R_t$ with the predetermined value, $R_t$ corresponding to the flow rate of liquid supplied to the capillary tube.

24. A method of manufacturing fluid vaporizing devices, comprising:

a) making a first fluid vaporizing device by:

i) metallurgically bonding a first electrode to a stainless steel capillary tube, the capillary tube having a length L1, an inlet, an outlet, and a resistance Rc1; and ii) metallurgically bonding a second electrode to the capillary tube closer to the outlet of the capillary tube than the first electrode, the second electrode having a resistance Re1;

the first fluid vaporizing device being operable to produce vaporized fluid by supplying a liquid to the capillary tube through the inlet, and applying a voltage across the first electrode and second electrode to heat the liquid in the capillary tube to a sufficient temperature to form a vapor which exits the capillary tube through the outlet; and b) making a second fluid vaporizing device by:

i) metallurgically bonding a first electrode to a stainless steel capillary tube, the capillary tube having a length L2, an inlet, an outlet, and a resistance Rc2; and ii) metallurgically bonding a second electrode to the capillary tube closer to the outlet of the capillary tube than the first electrode, the second electrode having a resistance Re2 the second fluid vaporizing device being operable to produce vaporized fluid by supplying a liquid to the capillary tube through the inlet, and applying a voltage across the first electrode and second electrode to heat the liquid in the capillary tube to a sufficient temperature to form a vapor which exits the capillary tube through the outlet;

wherein the first fluid vaporizing device has a total hot resistance Rt1=Rc1+Re1 during delivery of the vaporized fluid, and a tuning range TR1≧10 mΩ which equals the difference of a maximum hot resistance value R1max and a minimum hot resistance value R1min at which the capillary tube can be heated to produce a desired quality aerosol; the second fluid vaporizing device has a total hot resistance $Rt2=Rc2+Re2$ during delivery of the vaporized fluid, and a tuning range $TR2 \geqq 10$ mΩ which equals the difference of a maximum hot resistance value R2max and a minimum hot resistance value R2min at which the capillary tube can be heated to produce a desired quality aerosol; the first and second fluid vaporizing devices having capillary tubes and/or second electrodes which are not identical in size, R1min and R2min are unequal, and/or R1max and R2max are unequal, the first and second fluid vaporizing devices having the same target resistance during operation thereof and the target resistance being within the range of R1min to R1max and within the range of R2min to R2max.

25. The method of claim 24, wherein TR1 and/or TR2 is at least 20 mΩ.

26. The method of claim 24, wherein the capillary tubes of the first fluid vaporizing device and second fluid vaporizing device have a length of at least 20 mm.

27. The method of claim 24, wherein the capillary tubes of the first fluid vaporizing device and second fluid vaporizing device have a length of at least 40 mm.

28. The method of claim 24, wherein the second electrodes of the first fluid vaporizing device and second fluid vaporizing device are made of stainless steel.

* * * * *